United States Patent [19]

Wagu et al.

[11] 4,438,106
[45] Mar. 20, 1984

[54] INCLUSION COMPOUND OF EICOSAPENTAENOIC ACID OR DOCOSAHEXAENOIC ACID WITH CYCLODEXTRIN

[75] Inventors: Masakatsu Wagu; Shoichiro Hayashi; Kouichi Kodama, all of Iwaki, Japan

[73] Assignee: Kureha Kagaku Kabushiki Kaisha, Tokyo, Japan

[21] Appl. No.: 393,314

[22] Filed: Jun. 29, 1982

[30] Foreign Application Priority Data

Jul. 16, 1981 [JP] Japan ................................. 56-111439

[51] Int. Cl.³ ............................................. A61K 31/70
[52] U.S. Cl. .................................... 424/180; 536/103; 424/361
[58] Field of Search .................. 424/180, 361; 536/103

[56] References Cited

U.S. PATENT DOCUMENTS 2,959,580 11/1960 Schlenk et al. ...................... 536/103
3,140,184 7/1964 Robbins et al. ...................... 536/103

FOREIGN PATENT DOCUMENTS 2037306 7/1980 United Kingdom ................ 424/180
1580201 11/1980 United Kingdom ................ 424/180
1590022 5/1981 United Kingdom ................ 424/180
2067583 7/1981 United Kingdom ................ 424/180

OTHER PUBLICATIONS

Chemical Abstract, vol. 82, No. 13, 1973, p. 508, Abstract No. 80217d, Miyao et al.
Chemical Abstract, vol. 91, No. 16, 1979, p. 353, Abstract No. 128963n, Jozsef et al.
Chemical Abstract, vol. 92, No. 31980, p. 645, Abstract No. 22061x, Jozsef et al.
Hermann Schlenk and Donald M. Sand, The Association of a-and B-Cyclodextrins with Organic Acids, 1961, pp. 2312-2320, J. Am. Chem. Soc. 83.
Hermann Schlenk, Donald M. Sand and Jerry Ann Tillotson, Stabilization of Autoxidizable Materials by Means of Inclusion, 1955, pp. 3587-3590, J. Am. Chem. Soc. 77.

Primary Examiner—Johnnie R. Brown
Assistant Examiner—Elli Peselev

[57] ABSTRACT

This disclosure describes an inclusion compound of cyclodextrin in which at least one guest compound selected from the group of eicosapentaenoic acid, docosahexaenoic acid and alkali metal salts and alkyl esters thereof is included.

4 Claims, No Drawings

INCLUSION COMPOUND OF EICOSAPENTAENOIC ACID OR DOCOSAHEXAENOIC ACID WITH CYCLODEXTRIN

The present invention relates to inclusion compounds of cyclodextrin in which at least one guest compound selected from the group consisting of eicosapentaenoic acid (hereinafter referred to as EPA), docosahexaenoic acid (hereinafter referred to as DHA) and the alkali metal salts and alkyl esters thereof are included, which are odorless and stable.

It is said that EPA and DHA contained naturally in liver oil and body oil of blue fishes such as sardines, mackerel, mackerel pikes, etc. and marine animals such as cuttlefishes, etc., have a function of reducing the level of cholesterol in human serum as large as 4 times that of linolic acid (for instance, refer to Journal of the Japan Oil Chemist's Soc., 12(5), 249–260, 1963). Also it has been recently reported that EPA, the esters, metal salts and amides thereof have a function of suppressing platelet-aggregation and accordingly, they can be used for prevention and treatment of cerebral thrombosis and myocardial infarction (for instance, refer to Lancet, 2, 117, 1978 and Japanese Patent Laying Open No. 1544/1980) and since then, EPA and DHA having such functions have come to be regarded as important substance.

As clear from the mentioned above, it is effective for preventing and treating the diseases of circulatory organs to eat the blue fishes and marine animals which contain EPA and DHA having the pharmacological activites. However, also in Japan, with the occidentalization of the dietary life, the number of people who do not fond of blue fishes has increased and on the other hand, the number of people of corpulent habit and patients suffering from diseases of circulatory organs due to lack of exercise and increase of caloric intake has increased.

Accordingly, although it is desirable to take EPA and DHA in any form, since the fish oil collected from the blue fishes, EPA and DHA isolated and purified from the fish oil and the purified EPA, DHA and alkali metal salts and esters thereof, not to mention the fresh blue fishes themselves, have an odor specific to fishes, it is difficult for not only those who do not like the blue fishes but also for ordinary persons to ingest directly EPA and DHA even if they are well-purified, and they dislike to take such an EPA and DHA. And so, it has been attempted to contain EPA and DHA in medicines and foodstuffs for dietetics.

However, EPA and DHA have not only the disagreeable odor but also have five or six carbon-to-carbon double bonds within their molecule and they are extremely unstable. Accordingly, EPA and DHA easily absorb oxygen in the air to become noxious peroxides which are further decomposed to various aldehydes and ketones.

Furthermore, EPA and DHA are respectively an unstable fatty acid which produces noxious, cyclic or polymeric compounds by the action of light, heat and oxygen and moreover, their double bonds dislocate. In the case of making EPA or DHA contained in medicines and foodstuffs, accordingly, it is necessary to sield the light naturally, and to treat them in a flow of an inert gas such as gaseous nitrogen or carbon dioxide. For the long term storage of EPA and DHA, it is necessary to keep them at a low temperature of lower than 0° C. while diluting them with an inert solvent such as hexane, and according to circumstances, it becomes necessary to add an antioxidant such as tocopherol and the like.

It is an object of the present invention to provide a process for deodorizing and stabilizing EPA and DHA while retaining their useful activities mentioned above.

The aforementioned object can be attained according to the present invention by converting EPA or DHA into the respective inclusion compound with cyclodextrin.

The inclusion compound according to the present invention is prepared as follows:

One to two parts by weight of at least one guest compound selected from the group consisting of EPA, DHA, their alkali metal salt such as sodium salt or potassium salt and their alkyl ester such as methyl-, ethyl-, propyl- or butyl- esters and 5 to 10 parts by weight of cyclodextrin are dissolved in a solvent by heating in a flow of an inert gas, and the solution is slowly cooled while stirring to precipitate an inclusion compound of cyclodextrin in which the guest compound is included (caged) as a white solid. In this case of cooling the solution, it is preferable to adopt a cooling rate of 0.1° to 0.5° C./min, more preferably, of 0.2° to 0.3° C./min to avoid the precipitating of cyclodextrin without including the guest compound. And, as the solvent mentioned above, an aqueous alcoholic solution containing 40 to 80% by volume, preferably 60 to 70% by volume of metanol or ethanol is advantageously usable. However, a solvent which dissolves both the guest compound (EPA, DHA, or alkali metal salts and alkyl esters thereof) and cyclodextrin and in which the solubility of cyclodextrin depends largely on the temperature, for instance, acetone and tetrahydrofuran, can be used instead of the aqueous alcoholic solution.

Subsequently, the precipitated product is collected by filtration, washed with the solvent and dried to be a white, odorless, non-sticky and powdery substance.

The thus obtained product has varied composition according to the reaction conditions, however, under preferable conditions, about 85 to 98% by weight of the product is occupied by the inclusion compound of the guest compound with cyclodextrin (i.e., the inclusion compound according to the present invention) and the rest is composed of 1 to 15% by weight of free cyclodextrin without including the guest compound and 0.1 to 0.5% by weight of the guest compound which is present in a state of adhering to the surface of cyclodextrin. The content of the guest compound included in the inclusion compound is 4 to 15% by weight.

The white powdery substance produced as above can be used as it is for preparing the medicines or the foodstuffs, however, in the case where the contamination of free cyclodextrin is not desirable, it is easily removable because it is highly soluble in water.

In addition, although the guest compounds such as EPA and DHA are obtained ordinarily from the mixture of fatty acids prepared by saponifying the natural fish oil, for instance, sardine oil, followed by isolation and purification, the mixture of fatty acids may be brought into an inclusion compound as it is. In such a case, the composition ratio of the mixture of fatty acid remains as it is in the inclusion compound. The product prepared by using the natural mixture of fatty acids is also a white powdery substance without odor, and can be used as the raw material for preparing medicines and foodstuffs. Accordingly, in the production of the inclusion compound, it is not always necessary to isolate and purity the guest compound from the natural mixture of fatty acids obtained by saponification of sardine oil and the like.

Although, as has been stated, EPA and DHA are unstable to oxygen in the air and form peroxides with the oxygen, the guest compound such as EPA and DHA included in cyclodextrin scarcely absorb gaseous oxygen while being extremely stabilized. And, even in the reduction by gaseous hydrogen in the presence of Wilkinson's catalyst, the inclusion compound of guest compound with cyclodextrin was not reduced under the same condition as in the case of free guest compound wherein all the carbon-carbon double bonds have been reduced. These facts imply that the double bonds of guest compound which has been included (caged) in cyclodextrin are completely protected by cyclodextrin.

Thus, according to the present invention, the problem of stability caused by the double bonds in the molecule EPA and DHA has been solved by clathration, and the inclusion compound (clathrate) can be kept and treated in the air at room temperature as in the cases of ordinary substances. During its storage, there are no fear of exudation and isolation of the free and oily EPA or DHA from the inclusion compound. In addition, since the inclusion compound according to the present invention is purely white and odorless, it can be easily given a desired colour, smell and taste as well as shaped into various forms.

Moreover, the included guest compound, i.e., EPA, DHA or alkali metal salt and ester thereof in the inclusion compound according to the present invention can be easily recovered as the original guest compound by the following method. The inclusion compound is dissolved in a mixture of water and a water-soluble organic solvent, and the solution is subjected to extraction with a non-polar organic solvent such as hexane, benzene, toluene and the like. After distilling of the organic solvent from the organic layer of the extract, the original guest compound can be easily recovered. As the water-soluble organic solvent, methanol, ethanol, acetone, tetrahydrofuran are preferable, and the 1:1 by volume mixture of water and tetrahydrofuran is more preferable.

In addition, although it has been known that cyclodextrin forms inclusion compounds with various compounds, for instance, a medical compound such as prostagrandin, Vitamin A, chloramphenicol, etc. and an agricultural chemical such as dichlorvos, pyrethrin, etc., and the inclusion compounds of cyclodextrin in which the straight-chain saturated fatty acids or unsaturated fatty acids having less than three double bonds is included have also been known, the inclusion compound of cyclodextrin in which a fatty acid of more than 20 carbon atoms having more than 5 double bonds such as EPA and DHA is included has not hitherto been known.

The followings are the more detailed explanation of the present invention while referring to Examples, however, it should be understood that the scope of the present invention is never restricted to Examples shown as follows.

In the Examples, the word "fatty acid or esters thereof" means EPA, DHA or esters thereof itself in the case where a purified EPA, DHA or ester thereof is used for the preparation of the inclusion compound, and on the other hand, in the case where a mixture of fatty acids mainly containing EPA, DHA or esters thereof, it means the whole mixture.

Next, the method for analyzing the inclusion compound according to the present invention practically applied in the following Examples will be explained.

The crude inclusion compound prepared in a manner mentioned above contains the fatty acid or esters thereof adhered to the surface of cyclodextrin (referred to as "A" in Examples) and free cyclodextrin (referred to as "B" in Examples) together with the total fatty acid or ester thereof (referred to as "C" in Example). The percentages by weight of A, B and C, and the fatty acid or ester thereof which is truly included in the inclusion compound (referred to as "D" in Examples) are determined by the following method.

(A) Method of determination of "A":

After stirring 2 g of an exactly weight specimen in 30 ml of n-hexane to dissolve the adhered fatty acid or ester thereof, the residue was collected by filtration and washed with n-hexane, and n-hexane was distilled off under a reduced pressure from the combined filtrate and washings. Then, in the case where the fatty acid used as a raw material is a free acid, the residue is dissolved in 50 ml of aqueous 50% by volume ethanolic solution and the free acid is titrated with aqueous N/10 solution of sodium hydroxide. On the other hand, in the case where the raw material is an ester of fatty acid, the above-mentioned residue is dissolved in 10 ml of tetrahydrofuran, and the solution is subjected to gas chromatography under the following conditions.

Internal standard compound: 4,5,6,7-tetrachlorophthalide

Column: a glass column of 3 mm in internal diameter and 2 m in length, filled with DEGS-10%, 60 to 80 mesh Temperature: 200° C.

Carrier gas: Helium

Detector: FID detector (B) Method of determination of "B":

After stirring 2 g of an exactly weighed specimen in 30 to 100 ml of water to dissolve a free cyclodextrin in the specimen into water, the undissolved residue is collected by filtration, and washed with about 10 ml of water. The combined filtrate and washings are condensed under a reduced pressure and dried under a reduced pressure at 70° to 80° C. to be constant in weight. The amount of dried residue is weighed to find the content of the free cyclodextrin.

(c) Method of determination of "C":

After dissolving 1 g of an exactly weighed specimen in 150 ml of a 1:1 mixture of water and tetrahydrofuran completely, 30 ml of n-hexane is added to the solution while stirring well, and then 100 ml of water is further added to the mixture while stirring to extract the fatty acid or ester thereof into n-hexane. Extraction with each 30 ml of n-hexane is repeated 2 times more. After distilling off the n-hexane from the n-hexane layer under a reduced pressure, the same procedures are carried out as in "A" to determine the amount of the n-hexane extract.

(D) Method of determination of "D":

The amount by weight percentage of "D" is calculated according to the following formula:

$$D\ (\%\ \text{by weight}) = \frac{C - A}{100 - (A + B)} \times 100$$

PREPARATION OF THE INCLUSION COMPOUND

Example 1

Into 5 liters of aqueous 60% by volume methanolic solution consisting of 2.4 liters of methanol and 1.6 liters of water, 10.0 g of eicosapentaenoic acid of a purity of 99.3% by weight and 57 g of beta-cyclodextrin were added and the mixture was heated under a reflux condenser while stirring for about 60 minutes. On cooling the reaction mixture at a cooling rate of 0.2° C./min while stirring, an inclusion compound of eicosapentaenoic acid with beta-cyclodextrin was separated out. After cooling to 15° C. and stirring for 2 hours at the same temperature, the precipitate was collected by filtration, washed with about 100 ml of aqueous 60% by volume methanolic solution and dried under a vacuum on a water bath at 60° to 80° C. to be constant in weight. Thus, 58.4 g of the inclusion compound was obtained showing the following analytical data obtained by the analysis mentioned above:

| A | 0.3% by weight, |
| B | 5.4% by weight, |
| C | 9.0% by weight and |
| D | 9.2% by weight. |

Example 2

Into 4 liters of aqueous 70% by volume ethanolic solution consisting of 2.8 liters of ethanol and 1.2 liters of water, 15 g of methyl eicosapentaenoate of a purity of 92.5% by weight and 100 g of gamma-cyclodextrin were added and the mixture was heated under a reflux condenser while stirring for about 60 minutes. On cooling the reaction mixture at a cooling rate of 0.3° C./min while stirring, an inclusion compound of methyl eicosapentaenoate with gamma-cyclodextrin was separated out. After cooling to 15° C. and stirring for 3 hours at the same temperature, the precipitate was collected by filtration, washed with 150 ml of aqueous 70% by volume ethanolic solution and dried under a vacuum on a water bath at 60° to 80° C. to be constant in weight. Thus, 107 g of the inclusion compound was obtained showing the following analytical data:

| A | 0.2% by weight, |
| B | 8.5% by weight, |
| C | 9.3% by weight and |
| D | 10.0% by weight. |

Example 3

Into 4 liters of aqueous 70% by volume ethanolic solution consisting of 2.8 liters of ethanol and 1.2 liters of water, 15 g of ethyl docosahexaenoate of a purity of 95.8% by weight and 100 g of alpha-cyclodextrin were added and the mixture was heated under a reflux condenser while stirring for about 60 minutes. On cooling the reaction mixture at a cooling rate of 0.2° C./min while stirring, and inclusion compound of ethyl docosahexaenoate with alpha-cyclodextrin was separated out. After cooling to 15° C. and stirring for about 3 hours at the same temperature, the precipitate was collected by filtration, washed with about 150 ml of aqueous 70% by volume ethanolic solution and dried under a vacuum on a water bath at 60° to 80° C. to be constant in weight.

Thus, 105.2 g of the inclusion compound was obtained showing the following analytical data:

| A | 0.3% by weight, |
| B | 7.7% by weight, |
| C | 7.3% by weight and |
| D | 7.6% by weight. |

Example 4

Into 4 liters of aqueous 70% by volume ethanolic solution consisting 2.8 liters of ethanol and 1.2 liters of water, 20 g of a mixture of fatty acids, obtained by saponifying a natural sardine oil, containing 12.8% by weight of eicosapentaenoic acid and 7.6% by weight of docosahexaenoic acid and 100 g of betacyclodextrin were added and the mixture was heated under a reflux condenser while stirring for about 60 minutes. On cooling the reaction mixture at a cooling rate of 0.2° C./min while stirring, a crude inclusion compound was separated out. After cooling to 15° C. and stirring for about 3 hours at the same temperature, the precipitate was collected by filtration, washed with 150 ml of aqueous 70% by volume ethanolic solution and dried under a vacuum on a water bath at 50° to 60° C. to be constant in weight. Thus, 102.8 g of the inclusion compound was obtained showing the following analytical data:

| A | 0.6% by weight, |
| B | 5.5% by weight, |
| C | 11.7% by weight and |
| D | 11.8% by weight. |

Into 2 liters of a 2:3 by weight mixture of tetrahydrofuran and water, 20 g of the thus obtained inclusion compound was added to be dissolved by stirring. After the dissolution of the inclusion compound, 300 ml of hexane was added to the solution and the mixture was well stirred and then 2 liters of water was added to the mixture followed by stirring. Then the supernatant hexane layer was removed, and the aqueous phase was extracted with each 300 ml of hexane two times. The hexane extracts were combined, washed with water and dried on anhydrous sodium sulfate. By distilling off hexane from the dried extract under a reduced pressure, 2.3 g of oily pale yellow substance was obtained. After methylating the oily substance by adding it into 100 ml of methanol and adding a few drops of concentrated sulfuric acid while heating under a reflux condenser for 2 hours, 30 ml of water was added to the reaction mixture, and the mixture was extracted three times with each 50 ml of hexane. The hexane extracts were combined, dried on anhydrous sodium sulfate and subjected to distillation under a reduced pressure to obtain 1.8 g of methyl ester of the mixture of fatty acids. By subjecting the reaction product to gas chromatography mentioned before, it was found that the composition ratio of fatty acids of the ester obtained was the same as that of the sardine oil used for preparing the methyl ester.

Example 5

Into 4 liters of aqueous 70% by volume ethanolic solution consisting of 2.8 liters of ethanol and 1.2 liters of water, 20 g of methyl ester of sardine oil-fatty acid containing 13.5% by weight of methyl eicosapentaenoate and 6.4% by weight of methyl docosahexaenoate (a mixture of methyl esters obtained by esterification with methanol of natural sardine oil) and 100 g of beta-cyclodextrin were added and the mixture was heated under a reflux condenser while stirring for about 60 minutes. On cooling the reaction mixture at a cooling rate of 0.2° C./min while stirring, the crude inclusion compound was separated out. After cooling to 15° C. and stirring for about 3 hours at the same temperature, the precipitate was collected by filteration, washed with aqueous 70% by volume ethanolic solution and dried under a vacuum on a water bath at 50° to 60° C. to be constant in weight. Thus, 104.2 g of the inclusion compound was obtained showing the following analytical data:

| A | 0.2% by weight, |
| B | 6.4% by weight, |
| C | 12.5% by weight and |
| D | 13.2% by weight. |

Into 2 liters of a 2:3 by volume mixture of tetrahydrofuran and water, 20 g of the thus obtained inclusion compound was added, and then after adding 300 ml of hexane to the solution while stirring, 2 liters of water was further added to the mixture to carry out extraction. The extraction was repeated two times with each 300 ml of hexane, and the hexane extracts were combined, washed with water and dried on anhydrous sodium sulfate. By distilling off hexane from the dried extract under a reduced pressure, 2.5 g of pale yellow oily substance was obtained. As a result of subjecting the oily substance to gas chromatographic analysis mentioned before, the weight ratio of fatty acids contained in the inclusion compound was found to be identical with the composition of fatty acids of the sardine oil used in this Example.

Example 6

Into 100 ml of ethanol and 60 ml of water, 4.0 g of sodium eicosapentaenoate of a purity of 99.2% by weight and 10 g of beta-cyclodextrin was added and the mixture was heated under a reflux condenser while stirring for about 60 minutes. On cooling the reaction mixture at a cooling rate of 0.2° C./min while stirring, a crude inclusion compound was separated out. After cooling to 15° C. and stirring at the same temperature for about 3 hours, the precipitate was collected by filtration, washed with 30 ml of aqueous 67% by volume ethanolic solution and dried under a vacuum a water bath at 50° to 60° C. to be constant in weight. Thus, 10.0 g of an inclusion compound was obtained. On adding 28 ml of tetrahydrofuran and 42 ml of water to 2.2432 g of the thus obtained inclusion compound and carrying out the titration with aqueous N/10 hydrochloric acid solution, it was found that the amount of sodium eicosapentaenoate contained in the inclusion compound was 4.4% by weight.

STABILITY TEST

Example 1

The amount of oxygen absorbed by the respective inclusion compounds according to the present invention at 35° C. was determined by using a Warburg's manometer as the time passed by. The results are shown in Table 1.

As is seen in Table 1, the inclusion compound according to the present invention did not substantially absorb oxygen, in other words, was scarcely oxidized.

TABLE 1

| Specimen | Amount (mg) | unit: microliter Amount of absorbed oxygen after hours of | | | |
|---|---|---|---|---|---|
| | | 24 | 72 | 120 | 168 |
| Eicosapentaenoic acid | 120 | 7.2 | 13.0 | 16.1 | 17.5 |
| Inclusion compound of Example 1 | 1333.3 | 0.2 | 0.4 | 0.4 | 0.4 |
| (as eicosapentaenoic acid) | (120) | | | | |
| Methyl eicosapentaenoate | 120 | 7.5 | 13.9 | 16.6 | 18.0 |
| Inclusion compound of Example 2 | 1290.3 | 0 | 0.2 | 0.4 | 0.4 |
| (as methyl eicosapentaenoate) | (120) | | | | |
| Ethyl docosahexaenoate | 120 | 7.4 | 14.0 | 16.5 | 17.7 |
| Inclusion compound of Example 3 | 1643.8 | 0.2 | 0.2 | 0.2 | 0.2 |
| (as ethyl docosahexaenoate) | (120) | | | | |
| Fatty acid of sardine oil | 250 | 5.5 | 8.8 | 10.0 | 11.7 |
| Inclusion compound of Example 4 | 2136.8 | 0 | 0.2 | 0.3 | 0.4 |
| (as fatty acid of sardine oil) | (250) | | | | |
| Methyl ester of fatty acid of sardine oil | 250 | 5.7 | 9.3 | 10.3 | 12.2 |
| Inclusion compound of Example 5 | 2000.0 | 0 | 0.2 | 0.2 | 0.4 |
| (as methyl ester of fatty acid of sardine oil) | (250) | | | | |

Example 2

The respective inclusion compounds according to the present invention were subjected by hydrogenation at 24° C. by gaseous hydrogen in the presence of Wilkinson's catalyst, [Rh-P(C$_6$H$_5$)$_3$].

Each 1 g of the inclusion compounds of Examples 1 to 5 was added to 300 ml of benzene, and after adding 0.1 g of Wilkinson's catalyst to the mixture, gaseous hydrogen was passed through the mixture for about 4 hours to carry out hydrogenation. Then the benzene was distilled off under a reduced pressure from the reaction mixture, and after dissolving the residue in 150 ml of a 1:1 by volume mixture of tetrahydrofuran and water, and adding 50 ml of hexane and 100 ml of water to the solution, extraction was carried out. In the cases of the inclusion compounds of Examples 2, 3 and 5, the extract was condensed and subjected to gas chromatographic analysis under the same condition as before, and in the cases of the inclusion compounds of Examples 1 and 4, after distilling off the solvent from the extract under a reduced pressure, the extract was put into methanol, subjected to esterification by adding sulfuric acid and then subjected to gas chromatographic analysis.

As the results, it was found that the composition of the fatty acid in the original fatty acid mixture was kept unchanged in the inclusion compounds and that no reduction occurred in the hydrogenation step.

On the other hand, each of eicosapentaenoic acid, its methyl ester, ethyl docosahexaenoate, fatty acid of sardine oil and its methyl ester was subjected to hydrogenation under the same conditions as above and then subjected to gas chromatographic analysis to show that all carbon-to-carbon double bonds in each compound subjected to hydrogenation were reduced to give saturated fatty acid or ester thereof.

What is claimed is:

1. An inclusion compound of cyclodextrin and one or more compounds selected from the group consisting of eicosapentaenoic acid, docosahexaenoic acid, alkali metal salts thereof, and C$_1$ to C$_4$ alkyl esters thereof.

2. An inclusion compound according to claim 1, wherein the amount of said compound is 4 to 15% by weight of the total amount of said inclusion compound.

3. An inclusion compound according to claim 1, wherein said alkali metal is sodium or potassium.

4. An inclusion compound according to claim 1, wherein said cyclodextrin is alpha-, beta- or gamma-cyclodextrin.

* * * * *